US006194585B1

(12) United States Patent
Chiu et al.

(10) Patent No.: US 6,194,585 B1
(45) Date of Patent: Feb. 27, 2001

(54) PROCESS FOR PREPARING 5-LIPOXYGENASE INHIBITORS

(75) Inventors: Charles Kwon-Fung Chiu, Guilford; Ravi Mysore Shankar, Groton; Douglas J. M. Allen, New London, all of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/387,707

(22) Filed: Aug. 24, 1999

Related U.S. Application Data

(60) Provisional application No. 60/113,221, filed on Dec. 22, 1998.

(51) Int. Cl.$^7$ .................................................. C07D 233/02
(52) U.S. Cl. .......................................... 548/311.1; 514/397
(58) Field of Search ............................................ 548/311.1

(56) References Cited

U.S. PATENT DOCUMENTS 5,883,106 * 3/1999 Stevens et al. ...................... 514/277

FOREIGN PATENT DOCUMENTS

0462830 * 12/1991 (EP) .
0488602 *  6/1992 (EP) .
0505122 *  9/1992 (EP) .
0540165 *  5/1993 (EP) .

9429299 * 12/1994 (WO) .

* cited by examiner

*Primary Examiner*—Floyd D. Higel
(74) *Attorney, Agent, or Firm*—Peter C. Richardson; Paul H. Ginsburg; Jolene W. Appleman

(57) ABSTRACT

The present invention relates to the process for preparing a compound of the formula

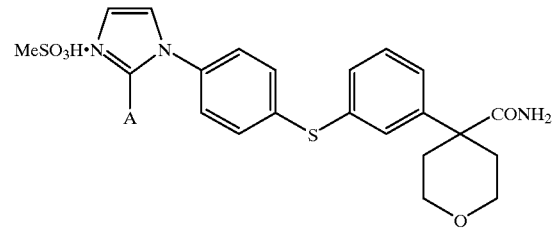

wherein A is $C_1$–$C_6$ alkyl, an aryl which is mono or disubstituted with F, Cl, Br, $OCH_3$, $C_1$–$C_3$ alkyl or benzy. In the preferred compound A is $CH_3$. The 5-lipoxygenase inhibitors that are prepared in accordance with the present invention are selective inhibitors of the action of lipoxygenase enzyme and are useful in the treatment or alleviation of inflammatory diseases, allergy and cardiovascular diseases in mammals.

25 Claims, No Drawings

PROCESS FOR PREPARING 5-LIPOXYGENASE INHIBITORS

This application claims the benefit of U.S. Provisional Application No. 60/113,221 filed Dec. 22, 1998.

BACKGROUND OF THE INVENTION.

This invention relates to the process and intermediates for preparing 5-lipoxygenase inhibitors. The 5-lipoxygenase inhibitors that are prepared in accord with the present invention are disclosed in U.S. Pat. No. 5,883,106 which is a continuation of 08/809,901 filed Jun. 13, 1997 now abandoned. This pending application is entitled "5-lipoxygenase Inhibitors" and is incorporated by reference in its entirety.

The 5-lipoxygenase inhibitors that are prepared in accord with the present invention are selective inhibitors of the action of lipoxygenase enzyme and are useful in the treatment or alleviation of inflammatory diseases, allergy and cardiovascular diseases in mammals.

SUMMARY OF THE INVENTION

The present invention relates to a process for preparing a compound of the Formula

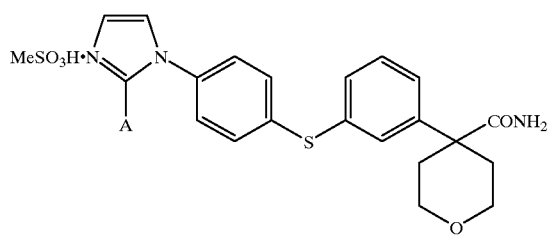

I wherein A is $C_1$–$C_6$ alkyl, an aryl, which is mono or disubstituted with F, Cl, Br, $OCH_3$, $C_1$–$C_3$ alkyl or benzyl, which comprises reacting a compound of the Formula

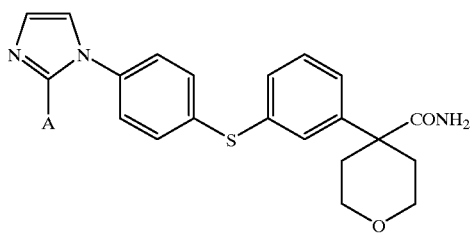

II wherein A is $C_1$–$C_6$ alkyl, an aryl, which is mono or disubstituted with F, Cl, Br, $OCH_3$, $C_1$–$C_3$ alkyl or benzyl, with a sulfonic acid in a $C_1$–$C_5$ alkyl alcohol; and precipitating the compound of Formula I by addition of an organic solvent that is less polar than the alcohol.

The acid is methanesulfonic acid and the organic solvent is diisopropyl ether or ethylacetate.

In a further aspect of the present invention, the compound of Formula II is prepared by reacting a compound of Formula

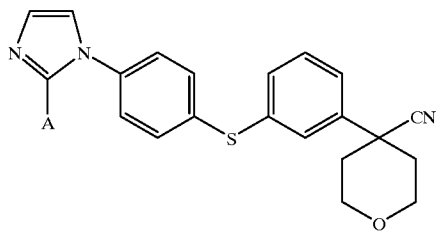

III wherein A is $C_1$–$C_6$ alkyl, an aryl, which is mono or disubstituted, with F, Cl, Br, $OCH_3$, $C_1$–$C_3$ alkyl or benzyl, with a hydroxide in an alcohol solvent.

The hydroxide is potassium hydroxide and the alcohol is tertiary butyl alcohol.

In a further aspect of the present invention, the compound of Formula III is prepared by reacting a compound of Formula

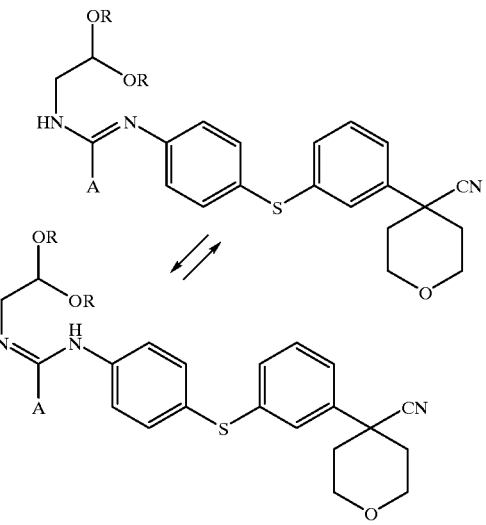

IV wherein A is $C_1$–$C_6$ alkyl, an aryl, which is mono or disubstituted with F, Cl, Br, $OCH_3$, $C_1$–$C_3$ alkyl or benzyl, with an organic or mineral acid.

The acid is acetic acid, sulfuric acid, formic acid or p-toluenesulfonic acid. The preferred acid is formic acid.

In a further aspect of the present invention, the compound of Formula IV is prepared by reacting the compound of Formula

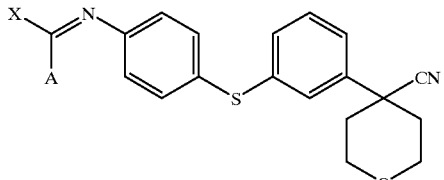

V wherein A is $C_1$–$C_6$ alkyl, an aryl, which is mono or disubstituted with F, Cl, Br, $OCH_3$, $C_1$–$C_3$ alkyl or benzyl and wherein X is Cl, Br, I, or $OCH_3$ with an excess of amino acetaldehyde acetal.

The amino acetaldehyde acetal is aminoacetaldehyde dimethylacetal or aminoacetaldehyde diethyl acetal In a further aspect of the present invention, the compound of Formula V wherein X is Cl, Br or I is prepared by reacting a compound of Formula

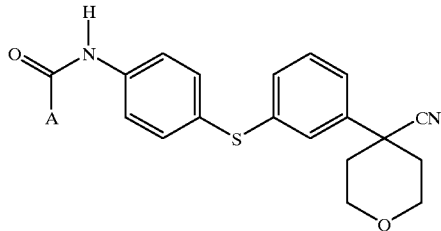

VI wherein A is $C_1$–$C_6$ alkyl, an aryl, which is mono or disubstituted with F, Cl, Br, $OCH_3$, $C_1$–$C_3$ alkyl or benzyl, with a phosphorous pentahalide in an inert solvent. The compound of Formula V may also be prepared by reacting a compound of Formula VI with $(CH_3)_3O^+BF_4^-$ to form an intermediate where x is $OCH_3$.

The pentahalide is phosphorous pentachloride, phosphorous pentaiodide or phosphorous pentabromide and the solvent is toluene. The preferred A is $CH_3$.

In a further aspect of the present invention, the compound of formula VI is prepared by the reacting of a compound of the Formula

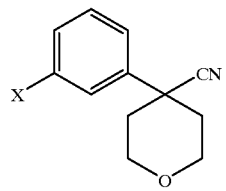

VIII wherein X is Cl, Br or I with an excess of 4-amino-thiopenol with a base in an inert solvent to give a compound of Formula

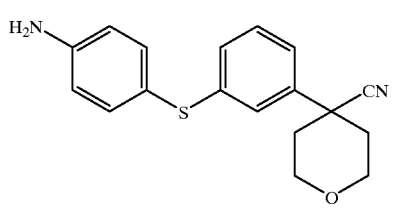

VII and further treating a compound of formula VII by acylation with an acid halide or anhydride.

Another more preferably way of preparing a compound of Formula VI is by reacting a compound of the Formula VIII

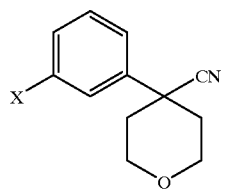

VIII wherein X is Cl, Br, or I with an excess of 4-amido-thiopenol with a base in an inert solvent.

The 4-amido thiophenol is 4-acetamido thiophenol The solvent is NMP or DMSO.

The base is sodium carbonate/cesium carbonate.

In a further aspect of the present invention, the compound of Formula VIII can be prepared by reacting a compound of Formula

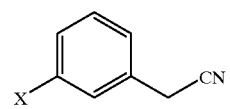

IX wherein X is Br, Cl or I with bis 2-chloroethyl ether, an alkaline base and a phase transfer catalyst in an inert solvent.

The phase transfer catalyst is tetrabutyl ammonium hydrogen sulfate. The base is sodium hydroxide.

The inert solvent is a mixture of tetrahydrofuran and water.

The invention also relates to a novel compound of the Formula

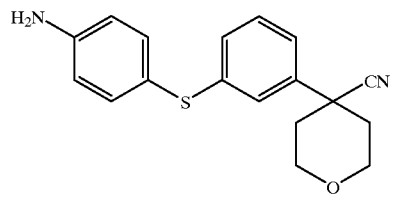

VII

The invention also relates to a novel compound of the Formula

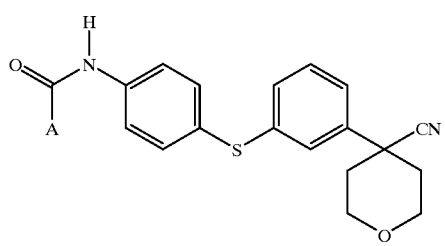

VI wherein A is $C_1$–$C_6$ alkyl, an aryl, which is mono or disubstituted with F, Cl, Br, $OCH_3$, $C_1$–$C_3$ alkyl or benzyl.

The invention also relates to a novel compound of the Formula

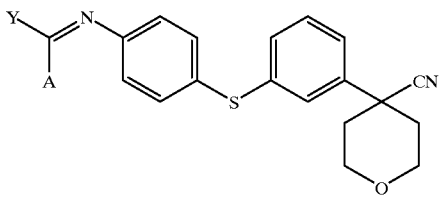

V wherein A is $C_1$–$C_6$ alkyl, an aryl, which is mono or disubstituted with F, Cl, Br, $OCH_3$, $C_1$–$C_3$ alkyl or benzyl and wherein X is I, Br, Cl or $OCH_3$.

The invention also relates to a novel compound of the Formula

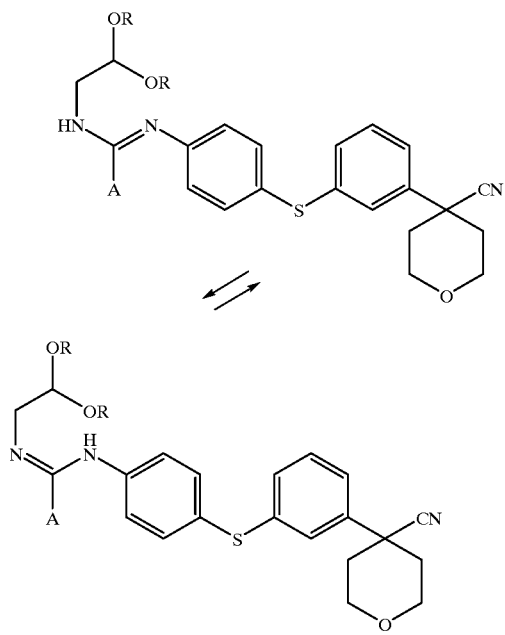

IV wherein A is $C_1$–$C_6$ alkyl, an aryl, which is mono or disubstituted with F, Cl, Br, $OCH_3$, $C_1$–$C_3$ alkyl or benzyl and wherein R is $C_1$–$C_6$ alkyl.

The invention also relates to a novel compound of the Formula

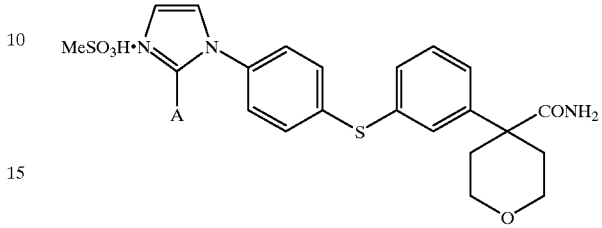

I wherein A is $C_1$–$C_6$ alkyl, an aryl, which is mono or disubstituted with F, Cl, Br, $OCH_3$, $C_1$–$C_3$ alkyl or benzyl.

A preferred compound is

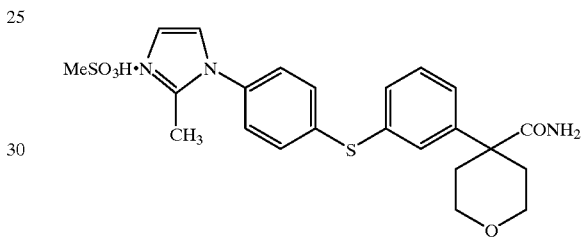

I

These novel compounds are used in the preparation of 5-lipoxygenase inhibitors and their pharmaceutical composition useful in the treatment or an alleviation of inflammatory diseases, allergy and cardiovascular diseases in mammals.

DETAILED DESCRIPTION OF THE INVENTION

The new process synthesis is shown in the Reaction Scheme 1 below

Scheme 1

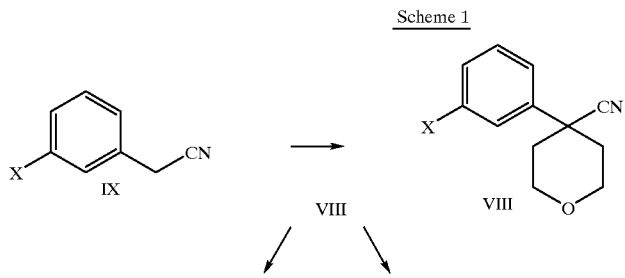

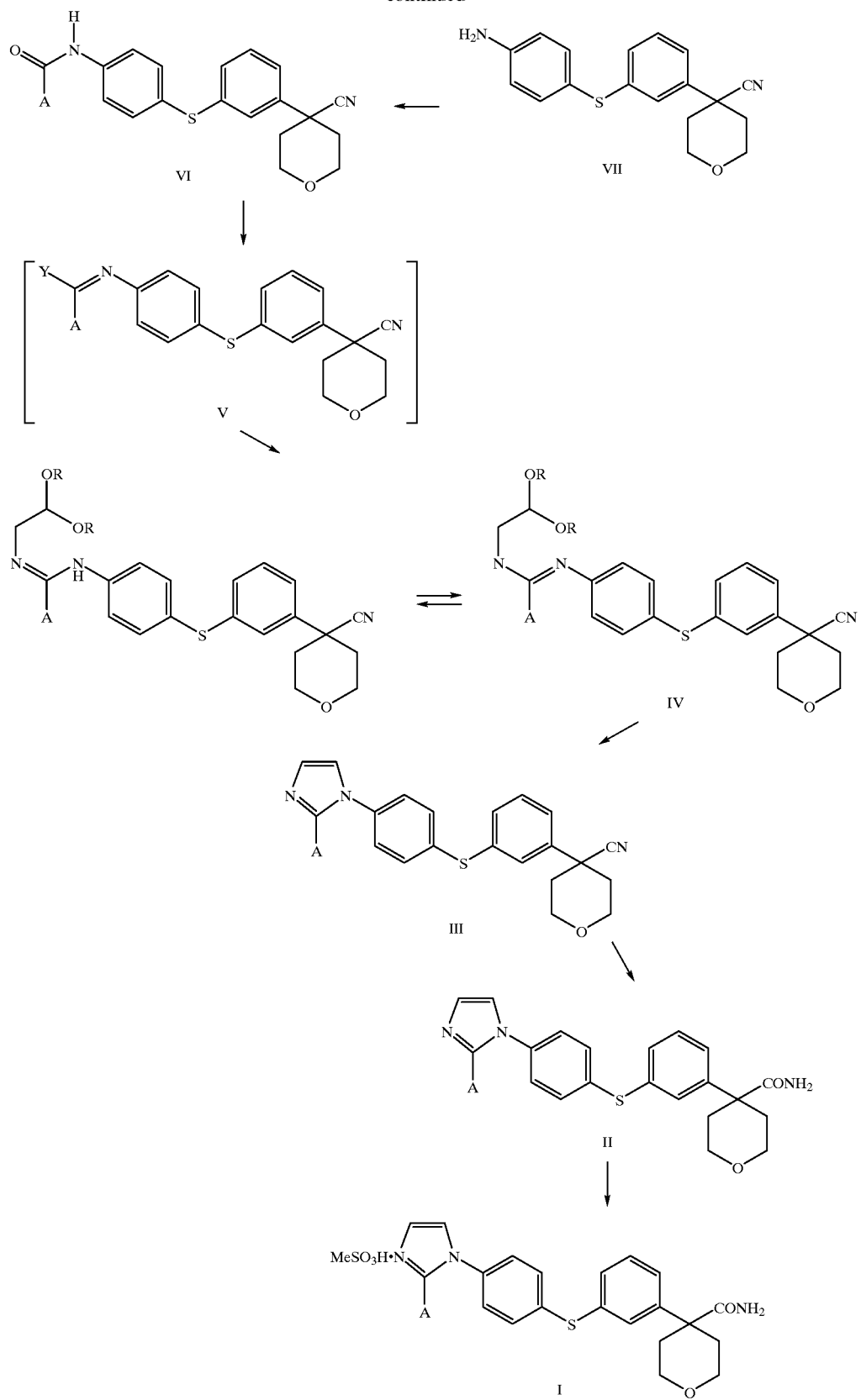

3-Bromophenyl acetonitrile in tetrahydrofuran is treated with aqueous NaOH, tetra butyl ammonium hydrogen sulfate and bis 2-chloro-ethyl ether to give the aryl bromide compound of Formula VIII.

The aryl bromide compound VIII is treated with either 4-aminothiophenol to give the aniline compound VII followed by acylation or with the 4-amidothiophenol to give the amide compound VI. The imidazole function is incorporated with transformation of the Formula VI amido group by heating compound VI with a phosphorous pentahalide to give the compound V which is treated with aminoacetaldehyde alkylacetal to provide the amidine compound IV. The amidine compound IV exists as a mixture of tautomers which are not isolated and are immediately subjected to acid-induced cyclization to provide the imidazole compound III. Subsequent hydrolysis of the nitrile function of the Imidazole compound III gives the 5-lipoxyygenase inhibitor compound II. The preferred salt form is found by treating compound II with methanesulfonic acid to give compound I.

The new process of the present invention eliminates the previous two expensive palladium (O) coupling reactions to introduce a sulfide linkage to the molecule as described in U.S. Pat. No. 5,883,106 incorporated by reference in its entirety. In addition the above preferred sulfur atom was previously introduced by means of a TIPS-thiol reagent (TIPS IS TRISOPROPYL SILYL), which is prepared from toxic hydrogen sulfide and expensive TIPS-chloride Compound I where A is $CH_3$ is the preferred salt form of a 5-lipoxygenase inhibitor that is useful in the treatment or alleviation of inflammatory diseases, allergy and cardiovascular diseases in mammals. In particular compound I is of use in the treatment or alleviation of inflammatory diseases.

These useful 5-lipoxygenase inhibitors can be administered in a wide variety of dosages form.

For treatment of the various conditions described above, the compounds and their pharmaceutically acceptable salts can be administered to a human subject either alone, or preferably in combination with pharmaceutically acceptable carriers or diluents in a pharmaceutical composition according to standard pharmaceutical practice. The compounds can be administered orally or parenterally in conventional fashion.

When the Compounds are administered to a human subject for the prevention or treatment of an inflammatory disease, the oral dose range will be from about 0.1 to 10 mg/kg, per body weight of the Subject to be treated per day, preferably from about 0.1 to 4 mg/kg, per day in single or divided doses. If parenteral administration is desired, then an effective dose will be from about 0.05 to 5 mg/kg per body weight of the subject to be treated per day. In some instances it may be necessary to use dosages outside these limits, since the dosages will necessarily vary according to the age, weight and response of the individual patient as well as the severity of the patient's symptoms and the potency of the particular compound being administered.

For oral administration, the compounds of the invention and their pharmaceutically acceptable salts can be administered, for example, in the form of tablets, powders, lozenges, syrups or capsules or as an aqueous solution or suspension. In the case of tablets for oral use, carriers which are commonly used include lactose and corn starch. Further lubricating agents such as magnesium stearate are commonly added. In the case of capsules, useful diluents are lactose and dried corn starch. When aqueous suspensions are required for oral use, the active ingredient is combined with emulsifying and suspending accents. If desired, certain sweetening and/or flavoring agents can be added. For intramuscular, intraperitoneal, subcutaneous and intravenous use, sterile solutions of the active ingredient are usually prepared and the pH of the solutions should be suitably adjusted and buffered. For intravenous use, the total concentration of solute should be controlled to make the preparation isotonic.

In addition, particularly for the treatment of asthma, the compounds of Formula I of this invention can be administered to a human subject by inhalation. For this purpose they are administered as a spray or mist, according to standard practice.

The present invention is illustrated by the following examples but is not limited to the details thereof.

EXAMPLE 1

4-(3-Bromo-phenyl)-tetrahydro-pyran-4-carbonitrile

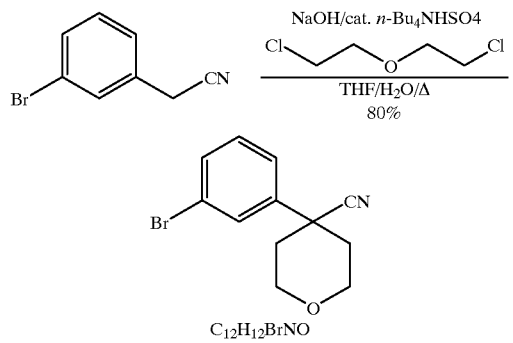

3-Bromophenylacetonitrile (51 g) in THF (300 mL) was treated with 40% aqueous NaOH (470 mL), tetrabutylammonium hydrogen sulfate (9 g) and dropwise addition of bis-2-chloroethyl ether (32 mL). The reaction mixture was heated under reflux for 4 hours and then cooled. The mixture was diluted with EtOAc (400 mL), washed with 5% HCl (200 mL), water (200 mL) and saturated $NaHCO_3$. After drying over $Mg_2SO_4$, solvent was removed to provide crude CP-399,554 as a waxy solid (75.4 g). The solid was slurried in a mixture of 1:1 isopropyl ether and hexanes (100 mL) to provide 4-(3-Bromo-phenyl)-tetrahydro-pyran-4-carbonitrile (55.3 g, 80% yield).

EXAMPLE II

4-[3-(4-Amino-phenyl sulfanyl)-phenyl]-tetrahydro-pyran-4-carbonitrile

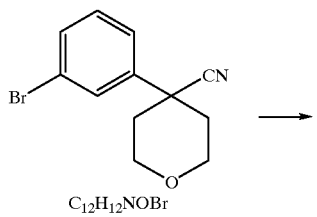

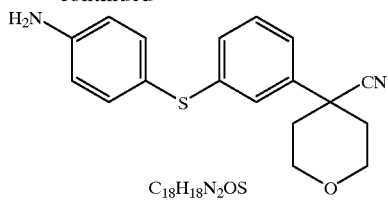

4-(3-Bromo-phenyl)-tetrahydro-pyran-4-carbonitrile (133.4 g), Na$_2$CO$_3$ (363.6 g), Cs$_2$CO$_3$ (223.1 g) and aminothiophenol (62.8 g) were heated in N-methyl pyrrolidinone (2.3 L) at 130° C. for 24 hours. More aminothiophenol (35.6 g) was added and heating was continued for another 8 hours. The mixture was cooled to room temperature, poured onto icewater (6.8 L) and filtered off. The product was suspended in water (2.5 L) filtered again and washed with water (1.5 L). The product was then slurried in EtOH (0.5 L), filtered off and dried at 40° C./20 mbar to yield 4-[3-(4-Amino-phenyl sulfanyl)-phenyl]-tetrahydro-pyran-4-carbonitrile (134.3 g, 86%).

EXAMPLE III

N-{4-[3-(4-Cyano-tetrahydro-pyran-4yl)-phenyl sulfanyl]-phenyl}acetamide 4-(3-Bromo-phenyl)-tetrahydro-pyran-4-carbonitrile (1.33 g) was mixed with Na$_2$CO$_3$ (1.59 g), Cs$_2$CO$_3$ (0.651 g) and 4-acetamidothiophenol (1 g) in N-methyl pyrrolidinone (15 mL). The reaction mixture was heated at 130° C. overnight. After cooling, the mixture was poured into iced water. The product precipitated out as a solid, was collected by suction filtration. The solid was recrystallized from a mixture of EtOAc and hexanes to provide N-{4-[3-(4-Cyano-tetrahydro-pyran-4-yl)-phenyl sulfanyl]-phenyl}acetamide(1.4 g, 80% yield).

EXAMPLE II AND III COMBINED

N-{4-[3-(4-Cyano-tetrahydro-pyran-4yl)-phenyl sulfanyl]-phenyl}acetamide

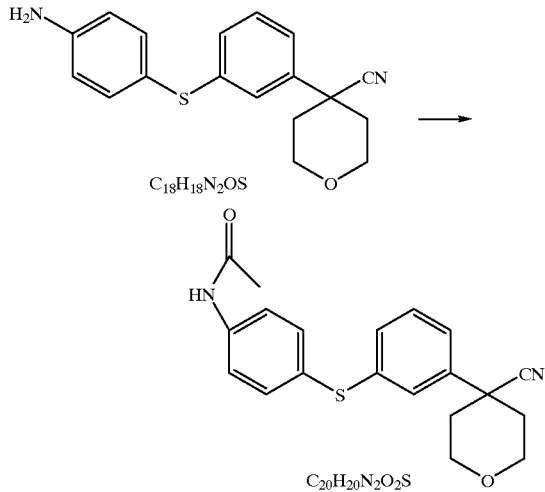

4-[3-(4-amino-phenyl sulfanyl)-phenyl]-tetrahydro-pyran-carbonitrile (93.57 g) and Et$_3$N (53.1 mL) were dissolved in EtOAc (1.23 L) and heated to 50–60° C. To this solution was added acetylchloride (27.7 ml) in EtOAc (73 mL) over 30 minutes. The suspension obtained was filtered and the filter cake was washed with EtOAc (3×150 mL). The combined EtOAc solutions were washed with water (0.5 L), half saturated aqueous Na$_2$CO$_3$ (2×0.5 L), water (0.5 L) and saturated aqueous NaCl (0.25 L). The organics were dried with Na$_2$SO$_4$ and evaporated at 40° C. The crude product was recrystallized from refluxing EtOH (0.52 L) to give after cooling, filtration and drying at 40° C./20 mbar, N-{4-[3-(4-Cyano-tetrahydro-pyran-4yl)-phenyl sulfanyl]-phenyl}acetamide (55.27 g, 52% yield).

EXAMPLE IV

4-{3-[4-(2-Methyl-imidazol-1-yl)-phenyl sulfanyl]-phenyl}-tetrahydro-pyran-4-carbonitrile

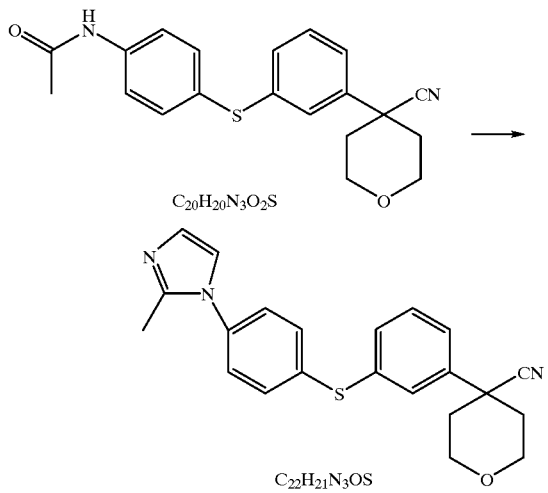

N-4-[3-(4-amino-phenyl sulfanyl)-phenyl]-tetrahydro-pyran-carbonitrile (49.77 g) was dissolved in toluene (545 mL) and heated to 60° C. under azetrope. From this solution, 20 mL of solvent were azeotroped off to remove remaining water. PCl$_5$, (35.0 g) was added in several portions to the solution. After stirring for 1 hour at 60° C., the solvent was distilled off. The residue was cooled to 10° C. and a mixture of Et$_3$N (19.8 mL) and aminoacetaldehyde dimethylacetal (15.2 mL) in EtOAc (500 mL) was added. The suspension obtained was stirred for 30 minutes at 10° C. and then more EtOAc (150 mL) was added. The mixture was washed with water (360 mL) followed by saturated aqueous NaCl (150 mL). The organics were dried with Na$_2$SO$_4$ (52 g) and evaporated at 50° C. The residue was dissolved in formic acid (250 mL) and heated to reflux for 1 hour. The reaction mixture was concentrated at 50° C./100 mbar to an oil. The oil was dissolved in 10% aqueous citric acid (400 mL) and EtOAc (200 mL). The aqueous layer was extracted with EtOAc (350 mL). The pH of the aqueous layer was adjusted to 9–10 with half-saturated K$_2$CO$_3$ solution (175 mL), and the solution was extracted with EtOAc (200 mL). The extract was dried with Na$_2$SO$_4$ (48 g) and evaporated at 50° C./100 mbar to give after filtration through a pad of silica using CH$_2$Cl$_2$/MeOH 10% as eluent, 4-{3-[4-(2-Methyl-imidazol-1-yl)-phenyl sulfanyl]-phenyl}-tetrahydro-pyran-4-carbonitrile (27.6 g, 55% overall yield).

EXAMPLE V

4-{3-[4-(2-Methyl-imidazol-1-yl)-phenyl sulfanyl]-phenyl}-tetrahydro-pyran-4-carboxylic acid amide

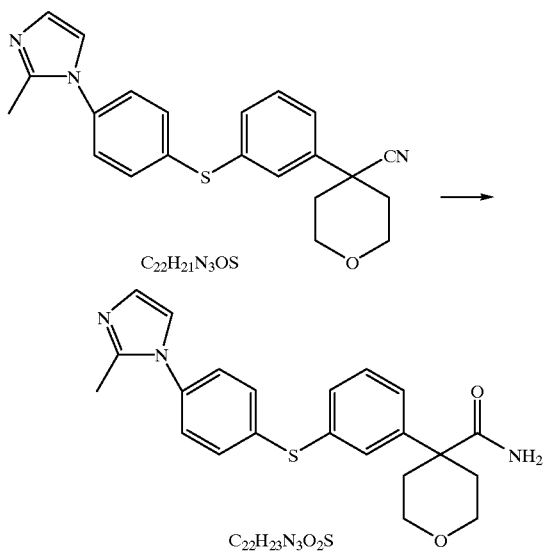

4-{3-[4-(2-Methyl-imidazol-1-yl)-phenyl sulfanyl]-phenyl}-tetrahydro-pyran-4-carbonitrile (27.35 g) were dissolved in t-BuOH (280 mL) at 50° C. To the solution, KOH (12.28 g) was added and the mixture was stirred overnight. The suspension was cooled to room temperature and water (180 mL) was added. The suspension obtained was filtered and the filtercake was dried at 50° C. to yield 4-{3-[4-(2-Methyl-imidazol-1-yl)-phenyl sulfanyl]-phenyl}tetrahydro-pyran-4-carboxylic acid amide (17.52 g, 55% yield).

EXAMPLE VI

4-{3-[4-(2-Methyl-imidazol-1-yl)-phenyl sulfanyl]-phenyl}-tetrahydro-pyran-4-carboxylic acid amide methyl sulfonate

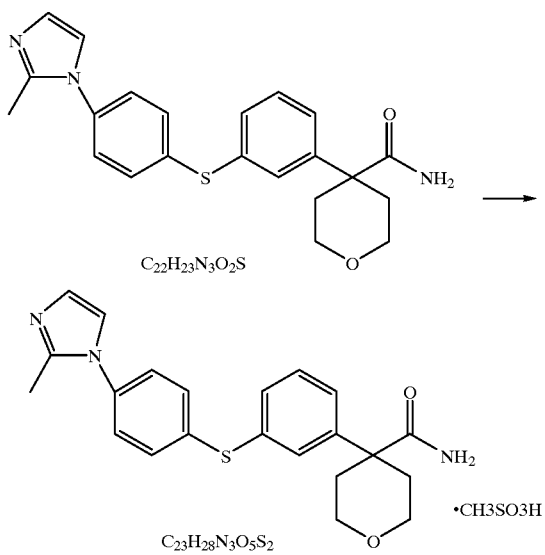

4-{3-[4-(2-Methyl-imidazol-1-yl)-phenyl sulfanyl]-phenyl}-tetrahydro-pyran-4-carboxylic acid amide (5.05 g) was suspended in MeOH (39 mL) at room temperature. To the suspension, methanesulfonic acid was added dropwise until all material was dissolved. The solution obtained was filtered, and the filter was washed with MeOH (20 mL). The combined MeOH solutions were treated with diisopropylether (280 mL) at room temperature. Upon stirring overnight crystals formed, which was collected by filtration and dried at 40° C./19 mbar to yield 4-{3-[4-(2-Methyl-imidazol-1-yl)-phenyl sulfanyl]-phenyl}-tetrahydro-pyran-4-carboxyl acid amide methyl sulfonate (4.85 g, 77% yield).

What is claimed is:

1. A process for preparing a compound of the Formula

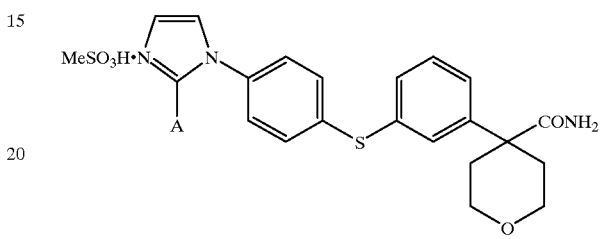

I wherein A is $C_1$–$C_6$ alkyl, an aryl, which is mono or disubstituted with F, Cl, Br, $OCH_3$, $C_1$–$C_3$ alkyl or benzyl a. comprising reacting a compound of the Formula

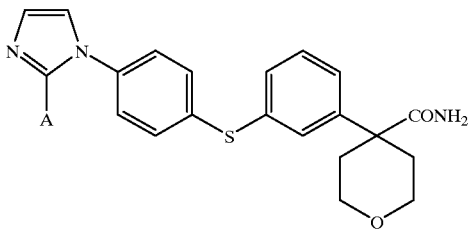

II wherein A is $C_1$–$C_6$ alkyl, an aryl, which is mono or disubstituted with F, Cl, Br, $OCH_3$, $C_1$–$C_3$ alkyl or benzyl, with a methanesulfonic acid in a $C_1$–$C_5$ alkyl alcohol; and b. precipitating the compound of Formula I by addition of an organic solvent whose polarity is less than said alcohol.

2. The process according to claim 1 wherein the organic solvent is diisopropyl ether or ethylacetate.

3. The process of claim 1 wherein said compound of Formula II is prepared by reacting a compound of Formula

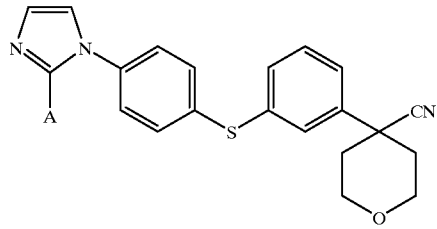

III wherein A is $C_1$–$C_6$ alkyl, an aryl, which is mono or disubstituted with F, Cl, Br, $OCH_3$, $C_1$–$C_3$ alkyl or benzyl with sodium or potassium hydroxide in an alcohol solvent.

4. The process according to claim 3 wherein the hydroxide is potassium hydroxide.

5. The process according to claim 3 where the alcohol is tertiary butyl alcohol.

6. The process according to claim 3 wherein said compound of Formula III is prepared by reacting a compound of Formula

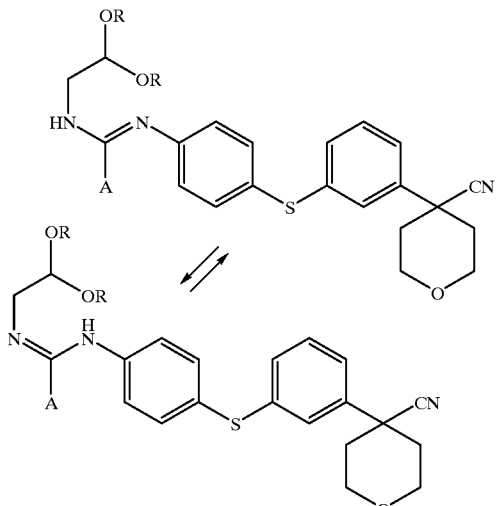

IV wherein A is $C_1$–$C_6$ alkyl, an aryl, which is mono or disubstituted with F, Cl, Br, $OCH_3$, $C_1$–$C_3$ alkyl or benzyl, with an organic or mineral acid.

7. The process according to claim 6 wherein the acid is acetic acid, sulfuric acid, formic acid or p-toluenesulfonic acid.

8. The process according to claim 7 wherein the acid is formic acid.

9. The process according to claim 6 wherein said compound of Formula IV is prepared by reacting the compound of Formula

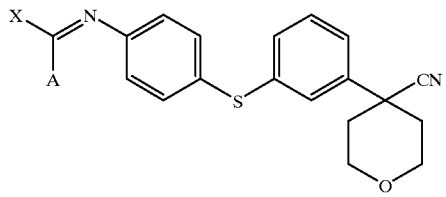

V wherein A is $C_1$–$C_6$ alkyl, an aryl, which is mono or disubstituted with F, Cl, Br, $OCH_3$, $C_1$–$C_3$ alkyl or benzyl, and wherein X is Cl, Br, I or $OCH_3$ with an excess of amino acetaldehyde acetal.

10. The process according to claim 9 wherein the amino acetaldehyde acetal is aminoacetaldehyde dimethylacetal or aminoacetaldehyde diethyl acetal.

11. The process according to claim 9 wherein said compound of Formula V wherein X is Cl, Br or I is prepared by reacting a compound of Formula

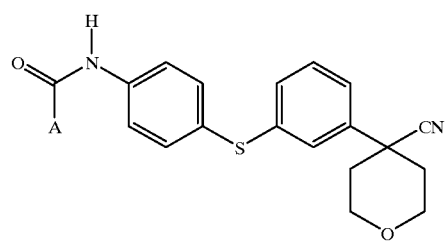

VI wherein A is $C_1$–$C_6$ alkyl, an aryl, which is mono or disubstituted with F, Cl, Br, $OCH_3$, $C_1$–$C_3$ alkyl or benzyl with a phosphorous pentahalide in an inert solvent.

12. The process according to claim 11 wherein the pentahalide is phosphorous pentachloride, phosphorous pentaiodide or phosphorous pentabromide and the solvent is toluene.

13. The process according to claim 11 wherein said compound of Formula VI is prepared by the reacting a compound of the Formula

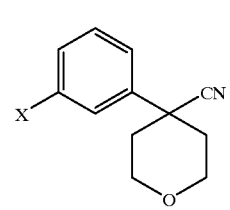

VIII wherein X is Cl, Br or I with an excess of 4-aminothiopenol and a base in an inert solvent to give a compound of Formula

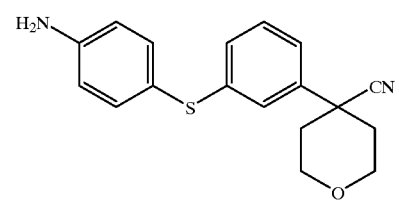

VII and acylating a compound of formula VII with an acid halide or anhydride.

14. The process according to claim 13 wherein the acylating agent is acetyl chloride.

15. The process according to claim 11 wherein said compound VI is prepared by reacting a compound of the Formula VIII

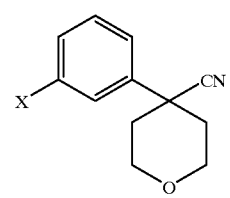

VIII wherein X is Cl, Br, or I with an excess of 4-amidothiophenol with a base in an inert solvent.

16. The process according to claim 15 wherein the 4-amido thiophenol is 4-acetamido thiophenol.

17. The process according to claim 15 wherein the base is N-methyl-2pyrrolidone and dimethyl sulfoxide.

18. The process according to claim 15 wherein the base is sodium carbonate/cesium carbonate.

19. The process according to claim 13 wherein the base is sodium carbonate/cesium carbonate.

20. The process according to claim 13 wherein said the solvent is N-methyl-2-pyrrolidone and dimethyl sulfoxide or NMP.

21. The process according to claim 15 wherein said compound of Formula VIII is prepared by reacting a compound of Formula

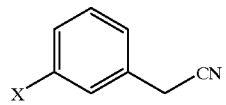

IX wherein X is Br, Cl or I with bis 2-chloroethyl ether, an alkaline base and a phase transfer catalyst in an inert solvent.

22. The process according to claim 21 wherein the inert solvent is a mixture of tetrahydrofuran and water, the base is sodium hydroxide and the phase transfer catalyst is tetrabutyl ammonium hydrogen sulfate.

23. A compound of the Formula

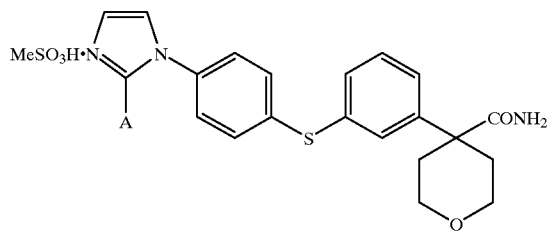

I wherein A is $C_1$–$C_6$ alkyl, an aryl, which is mono or disubstituted with F, Cl, Br, $OCH_3$, $C_1$–$C_3$ alkyl or benzyl.

24. A compound of the Formula

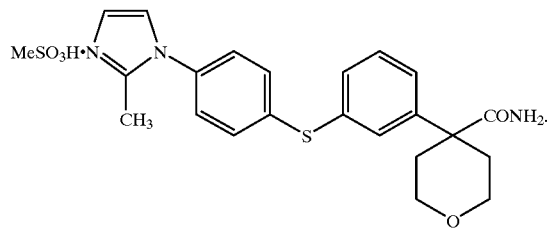

I

25. The process according to claim 9 wherein said compound of Formula V wherein X is Cl, Br, or I is prepared by reacting a compound of Formula VI

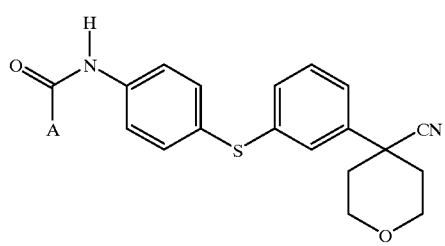

VI with $(CH_3)_3O^+BF_4^-$ to form a compound of formula

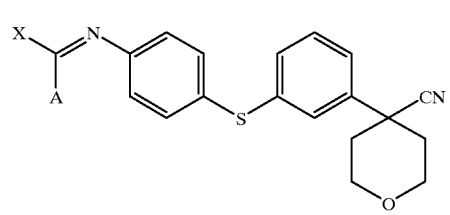

V wherein A is $C_1$–$C_6$ alkyl, an aryl, which is mono or disubstituted with F, Cl, Br, $OCH_3$, $C_1$–$C_3$ alkyl or benzyl and X is $OCH_3$.

* * * * *